United States Patent [19]

Shen et al.

[11] Patent Number: 5,356,773
[45] Date of Patent: Oct. 18, 1994

[54] GENERATION OF UNIDIRECTIONAL DELETION MUTANTS

[75] Inventors: Wenyan Shen; Mary M. Y. Waye, both of Toronto, Canada

[73] Assignee: Kinetic Investments Limited, Ontario, Canada

[21] Appl. No.: 762,735

[22] Filed: Sep. 17, 1991

Related U.S. Application Data

[63] Continuation of Ser. No. 352,335, May 16, 1989, abandoned.

[51] Int. Cl.$^5$ ............................................. C12Q 1/68
[52] U.S. Cl. .................................... 435/6; 435/91.1; 435/172.3; 435/320.1; 536/24.3
[58] Field of Search ............... 435/172.3, 51, 89, 6, 435/235, 252.3, 252.33, 320; 536/24.3; 935/31, 77

[56] References Cited

U.S. PATENT DOCUMENTS

| | | | |
|---|---|---|---|
| 4,521,509 | 6/1985 | Benkovic et al. | 435/172.3 |
| 4,582,788 | 4/1986 | Erlich | 435/172.3 |

FOREIGN PATENT DOCUMENTS

| | | | |
|---|---|---|---|
| 1230161 | 12/1987 | Canada | 435/172.3 |
| 1242657 | 10/1988 | Canada | 435/172.3 |

OTHER PUBLICATIONS

Hasan et al., "A Novel Multistep Method for . . . " Gene, 50 (1986) pp. 55–62.
Barcak et al. "A Method for Unidirectional Deletion Mutagenesis . . . " Gene, 49 (1986), pp. 119–128.
Waye et al. *Nucl. Acids Res.* vol. 13 pp. 8561–8571 1985 "EcoK selection vectors for shotgun cloning into M13 and deletion mutagenesis".
Carter et al. *Nucl. Acids Res.* vol. 13, pp. 4431–4443 1985 "Improved oligonucleotide site–directed mutagenesis using M13 vectors".
Poncz et al. *Proc Natl. Acad Sci* vol. 79 pp. 4298–4302 1982 "Nonrandom DNA sequence analysis in bacteriophage M13 by the dideoxy chain–termination method".

*Primary Examiner*—Richard A. Schwartz
*Assistant Examiner*—John Leguyader
*Attorney, Agent, or Firm*—Nixon & Vanderhye

[57] ABSTRACT

A novel method that allows introduction of unidirectional deletions into cloned DNA is described. This method is based on the use of a mixture of oligodeoxynucleotide primers that have fixed 5' (or 3') ends defining the end point of the deletion and variable 3' (or 5') ends composed of mixtures of all four nucleotides at six positions. The 5' ends of the oligodeoxynucleotides are hybridized to a fixed location of the M13K11RX templates and the 3' ends are hybridized randomly to the DNA to be analyzed. Such oligodeoxynucleotide primers when extended with DNA polymerase can direct deletions of intervening parts of the single-stranded DNA that by design contains multiple Eco K sites; the deletion products are selected on a host strain with the Eco K restriction system (e.g., using JM101 cells). This method is an efficient way of generating a nested set of deletion mutants useful for dideoxy-sequencing. It can also be used for creating a set of deletion mutants with a particular codon at the 5' or 3' end point.

21 Claims, 3 Drawing Sheets

GENERATION OF UNIDIRECTIONAL DELETION MUTANTS

This is a continuation of application Ser. No. 07/352,335, filed 16 May 1989, now abandoned.

FIELD OF THE INVENTION

This invention relates to the field of genetic engineering and genetic analysis, and more particularly to processes, reagents and kits for determining the chemical constitution of genetic material.

BACKGROUND OF THE INVENTION

The determination of nucleotide sequences in DNA material is fundamental to the field of genetic research and investigation, and to the synthesis of DNA materials. Methods currently used for this purpose, however, have technical limitations. For example, the well-established and widely practised Sanger dideoxy method for DNA sequencing relies upon generating randomly-terminated fragmental complements of the target DNA and electrophoretic separation of the fragments for analysis. Because of the limits on the sensitivity of the electrophoretic separation, the Sanger method is effectively limited in practice to sequencing of DNA samples having a maximum of about 500 nucleotide bases. Many genes of interest are longer than 500 bases in sequence.

Reducing the length of target DNA sequences inserted into M13 or plasmid vectors has become a routine step for deoxynucleotide sequence analysis. The commonly used methods involve deletion with exonucleases or restriction enzymes. Most of these methods require purification of double stranded or single stranded DNA, and sufficient knowledge of the restriction map of the target DNA to allow selection and use of a unique restriction site that is absent inside the target DNA.

It is an object of the present invention to provide a novel process for preparing deletion mutants of target DNA, useful in sequencing the DNA.

SUMMARY OF THE INVENTION

The present invention provides a process, and reagents for use therein, in which the DNA target material from which deletion mutants are to be obtained for sequencing is first inserted into a single strand producing plasmid or phage DNA which additionally contains a fixed anchor site comprising a sequence of at least five nucleotide bases of predetermined identity and sequence, a selection marker segment, and a priming site for DNA sequencing. The DNA material to be sequenced is inserted at a location upstream (or downstream) to, sequentially, the selection marker segment, the anchor site, and finally the priming site for sequencing. Then an oligonucleotide probe is applied to the construct containing the inserted DNA. The probe comprises a complex mixture of oligonucleotides, each component of the mixture having one end comprising nucleotide bases complementary in sequence with the at least five nucleotide bases of the anchor site, and an opposed end comprising a random sequence of at least 4 nucleotide bases in length.

Each oligonucleotide making up the probe accordingly binds strongly to the anchor site via their first end, and strongly to an individual, selected sequence on the inserted DNA being analyzed, a sequence corresponding to the random sequence of at least 4 nucleotide bases in length on the molecule of the probe. Because of the random nature of this opposed end sequence on the probe molecules, each such molecule may attach to a different region of the target DNA. Each probe molecule effectively bridges the selection marker.

Now the probe hybridized to the construct can be extended through DNA synthesis to result in deletion mutagenesis, a standard technique, to produce copies of the construct which omit the selection marker as well as the portion of the test DNA bridged by the probe. Cultivation of the resultant construct in appropriate cells and media will replicate and produce clones selecting for the absence of the selection marker, so that only constructs which have successfully accepted a probe are grown. Moreover, those in which the random sequence end of the probe has attached to portions of the vector extensively beyond the target DNA will be rejected by the cell.

As a result, there is selected a collection of clones each containing a different length of the DNA sequence under analysis. That length of the construct bridged by a probe molecule, which in each case is a portion comprising the selection marker and a random length of the target DNA sequence contiguous to the selection marker, has been deleted. The clones each contain a corresponding residual random portion of the DNA sequence under analysis, each of which has been randomly truncated at one end contiguous to the predetermined and hence recognizable anchor site residues. They also contain the priming site for sequencing.

The residual DNA sequences of the clones can be individually sequenced, along a conveniently sized portion of their DNA chain length, by the standard Sanger method of dideoxy sequencing, to determine the sequence of DNA under analysis, starting from the priming site and extending into the varyingly truncated target DNA. By providing a collection of differently truncated fragments of the originally inserted DNA, such a nested set of deletion mutants will enable sequencing of the target DNA starting at different positions, thereby helping to overcome the limitation of being able only to sequence about 500 residues or less. The deletion mutants can be distinguished from one another by electrophoresis, and a set selected for analysis which differ from one another by, say, 200–400 bases. Since each deletant carries the priming site for sequencing, the anchor site and a portion of the target DNA overlapping with that of the other deletants, one can determine the full sequence of the target DNA by determining the appropriate partial sequences of a properly selected group of the deletants so formed. One could for example start with undeleted target DNA, subject it to dideoxy sequencing and determine the sequence of the anchor site, followed by the sequence of the first, say, 250 bases of the target DNA closest to the anchor site. Next, one could take a deletant having 200 bases truncated, and on this determine the sequence of bases from numbers 200–450, the overlap of bases 200–250 in these first two deletants providing the required means for piecing together the sequence up to base 450. Next, a larger deletant having for example 380 bases truncated, and sequenced over the base portion 380–630, and so on, until the entire target DNA has been sequenced.

The deletion method of the invention can use M13 ss-DNA templates which are prepared the same way as for deoxynucleotide sequencing. Previous knowledge of the restriction map of the target DNA is not necessary. Furthermore, the end point of the deletion can be precisely determined, and thus the extent of the deletion is not dictated by the sequence of available restriction sites.

This is also a particularly useful method when making a nested set of truncated molecules with stop or start codons at one end. Thus the method can be used to create a set of deletion mutants with a particular codon at the 5' or 3' end. This is useful in producing specific proteins. The particular codon required, e.g. a stop codon TGA, is used as a sequence in the anchor site so that, after deletion mutagenesis according to the process of the invention, the stop codon is positioned adjacent to the inserted target DNA. From a start codon ATG in the target DNA to the stop codon so introduced is a known sequence of DNA encoding a protein of predetermined structure. Provided that the inserted stop codon is in appropriate reading frame, the protein will be produced by the DNA sequence. A truncated form of the unfused protein with a shortened carboxyl terminus end is thus encoded. Conversely, when cloned in the other orientation, an initiation codon, in place of the termination codon, in the same construct should be used. In this manner, a shortened unfused protein truncated from the amino terminus will be obtained. It is also possible to introduce any additional amino acids extended from the truncated proteins by using probes which have the appropriate codons inserted between the predetermined portion and the random portion of the probe. This technique is particularly useful for protein structure and function analysis.

From another aspect, the invention provides a kit for preparing deletion mutants from a target DNA material, and comprising:

an oligonucleotide probe comprising a complex mixture of oligonucleotides each having one end consisting of from 5-200 nucleotide bases of predetermined identity and sequence, and an opposed end comprising a random sequence of at least four nucleotide bases;

a plasmid or phage DNA containing, in sequential order, a priming site for initiation of sequencing, an anchor site consisting of a sequence of 5-200 nucleotide bases corresponding to the predetermined sequence of nucleotides on the probe, a selection marker sequence and at least one restriction site for insertion of target DNA;

viable bacterial cells incapable of tolerating the selection marker so as to permit cultivation therein of DNA omitting the selection marker but to prevent cultivation therein of DNA containing the selection marker.

BRIEF REFERENCE TO THE DRAWINGS

DESCRIPTION OF THE PREFERRED EMBODIMENTS

Figure 1:
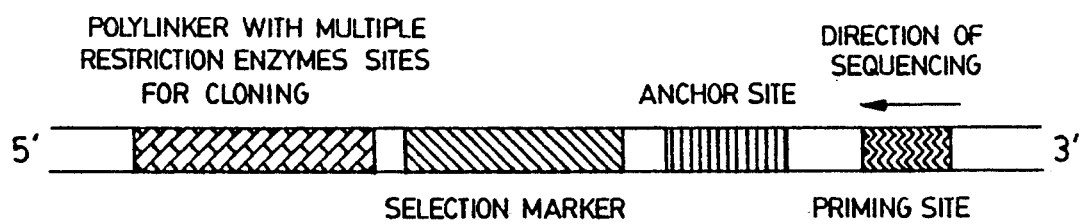
FIG. 1 is a diagrammatic representation of the arrangement of different sites on a construct for use in the present invention.

In the preferred arrangement according to the invention, the test DNA is inserted into suitable restriction sites located upstream of the selection marker which is thus upstream of the anchor site. The test DNA should not be inserted between the selection marker sequence and the anchor site, or the selection marker sequence will favour the selection of clones that have eliminated the entire test DNA sequence. However, the disposition of both the anchor site and the selection marker upstream from the inserted test DNA in the construct is possible and is within the scope of the present invention, although it is not preferred.

The oligonucleotide probe according to the preferred embodiment accordingly has its predetermined nucleotide sequence at its upstream, 5' end and its random nucleotide sequence at its downstream, 3' end.

One aspect of the present invention involves the use of a mixture of oligonucleotides with a fixed sequence of ten specific nucleotides at the upstream (5') end and a random sequence of at least four nucleotides at the downstream (3') end. Suitably the oligonucleotide has from about 10-20 total nucleotide bases, preferably 16. In general, the upstream end has at least 5 and preferably 6-10 nucleotides in specific sequence to match those of the anchor site for appropriate hybridization thereto. With 4 or fewer such nucleotides, there is too great a risk that the oligonucleotide probe will find other binding sites than the anchor site. It is Of course preferred that the anchor site has, correspondingly, 6-10 nucleotides in specific sequence to match those of the upstream end of the probe.

The downstream (3') end of the oligonucleotide probe has at least four and preferably six randomly sequenced nucleotide bases. The preferred oligonucleotide with its six random bases provides $4^6$ or 4096 different sequence combinations and substantially all of these are present in the probes used in the preferred embodiment of the present invention. This will provide probe molecules complementary to any stretch of six nucleotides along the entire length of target DNA, thus giving unrestrictedly different lengths of DNA fragments for proper analysis of the sequence.

The oligonucleotide probes thus preferably consist only of the aforesaid upstream end of 5-10 specific nucleotide bases in sequence, and the random downstream end of 4-6 random nucleotide bases. Accordingly, the most preferred probe for use in the present invention is an oligomer of 16 nucleotides bases, linked 5'-3', the 5' end thereof consisting of 10 nucleotide bases of predetermined selection and sequence, and the 3' end thereof consisting of six randomly selected and sequenced nucleotide bases. The precise choice of the 5'-end sequence is of course dictated by the sequence located on the construct between the selection marker segment and the priming site, and selected to be the anchor site.

The plasmid or phage DNA into which the DNA test material is inserted to make the construct can be any plasmid or phage DNA which is suitable for DNA sequencing. Thus the plasmid or phage DNA should be capable of accepting the gene or DNA sequence to be tested, by standard restriction and ligation techniques, and to replicate it in relatively large amounts in single stranded form. A specific example of a suitable phage is M13, which is commercially available, and of which a series of suitable variants, with various additional restriction sites, are also commercially available. Phagemid can also be used. Other examples of suitable filamentous sequencing vector plasmids and phages are commercially available and will be well known to those skilled in the art.

The selection marker segment of the construct is disposed between the anchor site and the target DNA, so that it is eliminated on replication by the presence of the probe. The selection marker may be any DNA sequence that causes toxicity to the host cell, so that constructs containing it cannot be replicated successfully in the host. Preferably, it is a genetic intolerance marker such as Eco K or Eco B, so that constructs containing it cannot be replicated in properly chosen cells such as appropriate strains of E. coli cells.

The method of the invention can be used to obtain deletion mutants from any gene or target DNA sequence which does not contain the same selection marker in its own right. Thus, when the construct contains Eco K as the selection marker, the method cannot be used as target genes which also have Eco K intolerance (about one per 16000 base pairs). Then another selection marker such as Eco B must be chosen.

FIG. 1 of the accompanying drawings diagrammatically shows the arrangements of various sites and sequences on a construct useful in the present invention. The test DNA is inserted by standard methods into the restriction enzymes sites of the polylinker sequence, so that the selection marker is disposed between the location of the target DNA and the anchor site at the time the oligonucleotide probe is hybridized thereto. The priming site is disposed beyond the anchor site, so that the priming site, anchor site and selection marker are sequentially arranged. In the preferred embodiment as shown, the target DNA is inserted at a location downstream from the selection marker.

Figure 2:
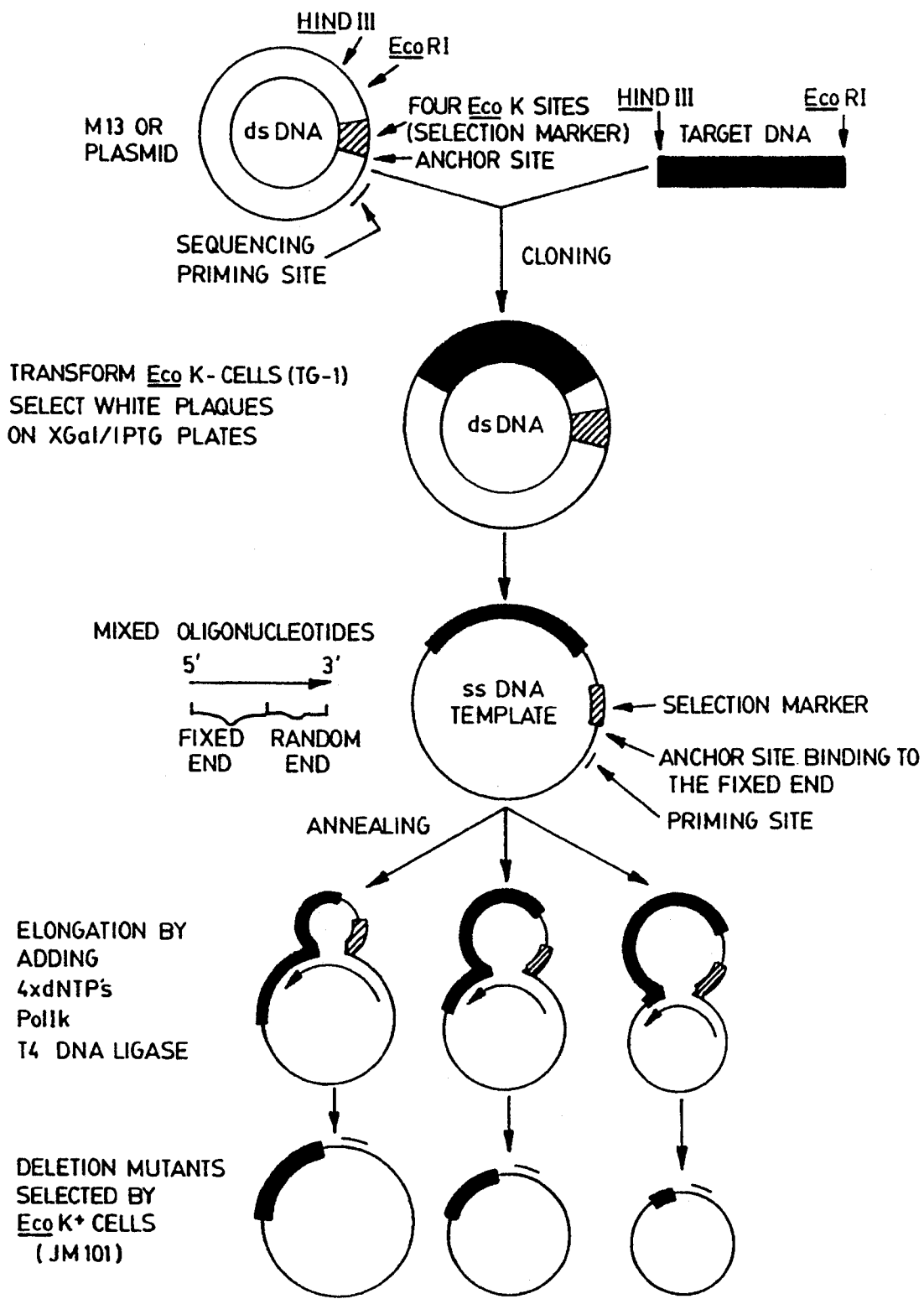
FIG. 2 is a diagrammatic representation of the process steps and sequence of the preferred embodiment of the invention.

Referring to the diagrammatic illustration of the process shown in FIG. 2, the starting M13 phage illustrated is M13K11RX which has four ECo K sites. It is prepared from TG1 cells which are Eco K (see Waye, M. M. Y; Verhoeyen, M. E.; Jones, P. J. and Winter, G; "Eco K selection vectors for shotgun cloning into M13 and deletion mutagenesis", Nucleic Acid Res. 13 (1985), 8561–8571). The target gene is cloned between Hind III and Eco RI sites of M13K11RX. The recombinant containing the target DNA can be selected by picking white plaques on Xgal/IPTG plates. DNA from the M13 recombinant phage is then prepared by growing in TG1 cells. Phosphorylated mutagenic oligodeoxynucleotide probes are then annealed to the template DNA. The heteroduplex is then put on ice, and four dNTPs, rATP, DTT, PolIk, T4 ligase added and incubated. Half the reaction is used to transform JM101 competent cells (prepared by the Hanahan 1983 method), to select against the parental clones with the four copies of Eco K sites.

The present invention thus provides an efficient way of obtaining a nested set of deletion mutants useful for deoxynucleotide sequencing. The strategy is based on the fact that a mixture of oligodeoxynucleotides (e.g. 16-mers) with a random nucleotide sequence at six positions of the 3' portion (5'-GGATCCCCTANNNNNN-3') can bind randomly at different positions on a DNA template (FIG. 2). The unidirectional nature of the deletion was achieved because the 5' portion of the oligodeoxynucleotide was designed to hybridize specifically to an anchor site upstream from the sequencing priming site while the 3' portion was designed to bind randomly on the target DNA. A schematic diagram of the method is shown in FIG. 2. This method is highly efficient because it selects against the parental M13K11 or M13K11RX recombinant template (with cloned target DNA insert and four copies of Eco K sites) when the mutagenized DNA is transfected into JM101, the host strain, which has the restriction enzyme Eco K.

One specific advantage of the system is that the single-stranded (ss) DNA that was used as the template can be prepared rapidly. There is no need to purify double-stranded (ds) RF DNA as in (a) the exonuclease III method (Guo et al., 1982), (b) the exonuclease III plus exonuclease VII method (Yanisch-Perton et al., 1985), (c) the BAL 31 method (Poncz et al., 1982) or (d) the exonuclease III plus S1 method (Henikoff, 1984). There is no need to purify ss DNA completely free of dNTPs as in the RD20 oligodeoxynucleotide-directed mutagenesis method (Dale et al., 1985).

Another specific advantage is that only two enzymes are needed: PolIk and T4 DNA ligase. Furthermore, the optimal amount of enzymes required does not have to be titrated exactly. This is quite different from other methods, e.g., the amounts of exonuclease III and VII ( Guo et al. , 1982; Yanisch-Perton et al. , 1985 ), S1 (Henikoff, 1984), DNase I (Hong, 1982) or T4 polymerase (Dale et al, 1985) have to be titrated carefully.

A further specific advantage is the end point of the deletion can be designed precisely using a mixture of oligodeoxynucleotides with fixed 5' as well as 3' portions. A corollary method also forming part of this invention generates mutants using oligodeoxynucleotides with fixed 3' ends and random 5' ends rather than random 3' ends. For the latter method, the gene of interest should be cloned 3' to the Eco K recognition sites, i.e, in the XhoI or SacI site of M13K11RX or the Eco RI site of M13K11 (Waye et al, 1985) and the extent of the deletion can be determined by the reverse sequencing method (Hong, 1981).

The invention is further described, for illustrative purposes, in the following specific examples.

MATERIALS (a) Enzymes, chemicals and radiochemicals

PolIk, ddNTPs, dNTPs, and T4 DNA ligase were obtained from Pharmacia-PL Biochemicals (Milwaukee, Wis.), [α -$^{32}$P] dATP for sequencing was obtained from New England Nuclear (Boston, Mass.). Oligodeoxynucleotides ( a mixture of 16-mers with the following sequences: 5'-GGATCCCCTANNNNNN-3') were obtained from Allelix (Mississauga, Canada).

(b) M13 phages and host strains

The constructions of M13K11RX and M13K11 , which have four Eco K sites, have been described previously (Waye et al., 1985). The tyrS gene from *Bacillus stearothermophilus* (1.7-kb HindIII-Eco RI fragment of tyrS gene; Waye and Winter, 1986) was cloned between the HindIII and EcoRI sites of M13K11RX; the histone H1-coding gene from *Xenopus laevis* (1.3-kb TaqI fragment of pXLHW7) was cloned into the AccI site of M13K11 (Turner et al., 1983); the histone H4-coding gene from *X. laevis* (2.3-kb PstI fragment of pXLHW7) was cloned into the PstI site of M13K11 (Moorman et al., 1981).

*Escherichia coli* TG1 was obtained from T. Gibson ( Gibson, 1984). E. coli TG1 has an inactive EcoK restriction system which supports growth of phages such as M13K11 and M13K11RX containing EcoK sites, while *E. coli* JM101 (Messing, 1979) has an active EcoK restriction system which restricts propagation of such phages. The presence of multiple EcoK sites makes the selection more efficient.

EXAMPLE 1 UNIDIRECTIONAL DELETION MUTAGENESIS OF M13 RECOMBINANTS

Step 1

The target DNA, namely the tyrS gene from *Bacillus stearothermophilus* (1.7kb HindIII-EcoRI fragment of tyrS gene; Waye and Winter, 1986), was eluted from an agarose gel and cloned into the appropriate restriction site( s ) in M13K11RX or M13K11. The recombinant DNA clones were selected by picking white plaques after transfecting TG1 cells in the presence of IPTG and XGal (Messing et al., 1977 ). To facilitate sequencing through the deletion junction, it is necessary to clone the target DNA such that the EcoK sites (selection marker) are in between the target DNA and the universal priming site. The genes were cloned into M13 in an orientation that depended on whether a nested set of 5' or 3' deletion mutants was required.

Step 2

The oligodeoxynucleotide-directed deletion procedure was performed as described by Carter et al. (1985). DNA templates used for mutagenesis were prepared as follows.

A single white plaque was picked into 10 ml of 2 x YT medium (0.8% Bacto tryprone, 0.5% Bacto yeast extract, 0.5% NaCl) with a 1/100-fold dilution of a fresh overnight culture of uninfected TG1 cells.

The phage inoculum was then incubated for 6 h at 37° C. with 220 rev./min agitation. The supernatant was collected and the phages were precipitated by adding 1/10 vol. of PEG (20% polyethyleneglycol + 2.5 M NaCl).

The pellets, each collected from 1 ml of the above supernatants, were dissolved in 50 $\mu$l TE buffer (10 mM Tris-HCl, pH 8.0, 0.1 mM EDTA), treated with RNase (0.1 mg/ml) at 37° C. for 20 min., extracted with 25 $\mu$l of phenol saturated with TE buffer and then extracted with ether to remove trace amounts of phenol.

The phage DNA was precipitated by adding 1/10 vol. of 3M Naacetate pH 5.5 and 2.5 vols. of ethanol.

The DNA pellet was dissolved in TE and the $A_{z260}$ was measured. For the mutagenesis experiment, 10 pmol of phosphorylated mutagenic primer were used per 1 $\mu$g of template DNA.

The above reaction mixture was transformed into JM101 using the method of Hanahan (1983). Only those phages which had lost all the EcoK sites were able to yield progenies. Approximately 100 plaques were obtained from 1 $\mu$g of ss-DNA template.

Step 3

Phage lysates were prepared and electrophoresed on a 0.7% agarose gel (Messing, 1983). Clones containing the appropriate deletions were then sequenced (Sanger et al. , 1977) .

EXAMPLES 2 AND 3

Using the same procedure, materials and quantities described in Example 1, deletion mutants containing fragments of the H1-coding gene from *Xenopus laevis* and the H4-coding gene from *X. laevis* were prepared from the respective starting materials as described.

From each of the three examples, a histogram was obtained from the number of clones recovered (vertical axis) and the different size deletion (horizontal axis) after oligodeoxynucleotide-directed deletion mutagenesis. These are shown on FIG. 3A, 3B and 3C Panel 'a' derives from parental clone M13 with the tyr S (1.7 kb) insert, Example 1. Panel 'b' is similarly derived from parental clone M13 with the H1(1.3kb) insert, Example 2. Panel 'c' is similarly derived from parental clone M13 with the H4(2.3 kb) insert. The sizes of the inserts were estimated by their mobility on 0.7% agarose gels. Sequencing data suggest that the mobility of M13 ss DNA is linear over the range of 0–2.3 kb insert sizes, and this method could resolve M13 clones which differed by 100 bp.

Figure 3A:
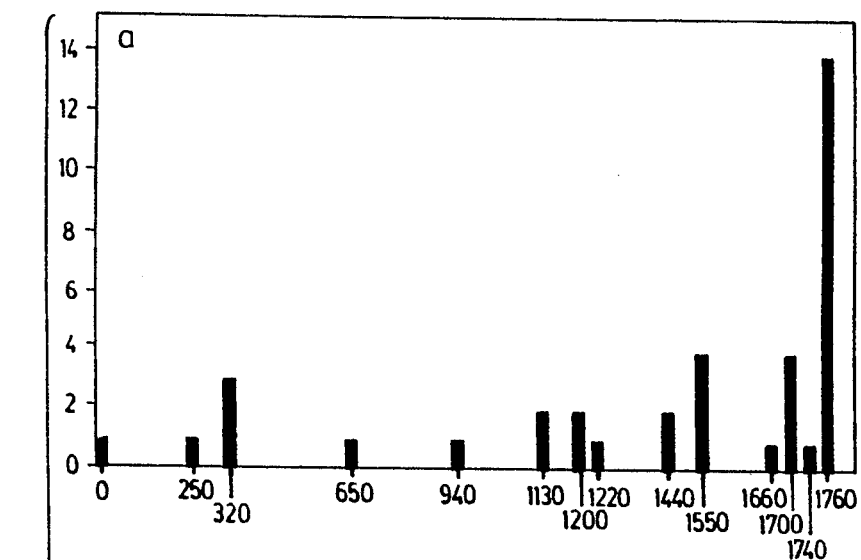
FIGS. 3A, 3B and 3C are histograms showing the number of clones with different size deletions, in accordance with the specific examples below.
Figure 3B:
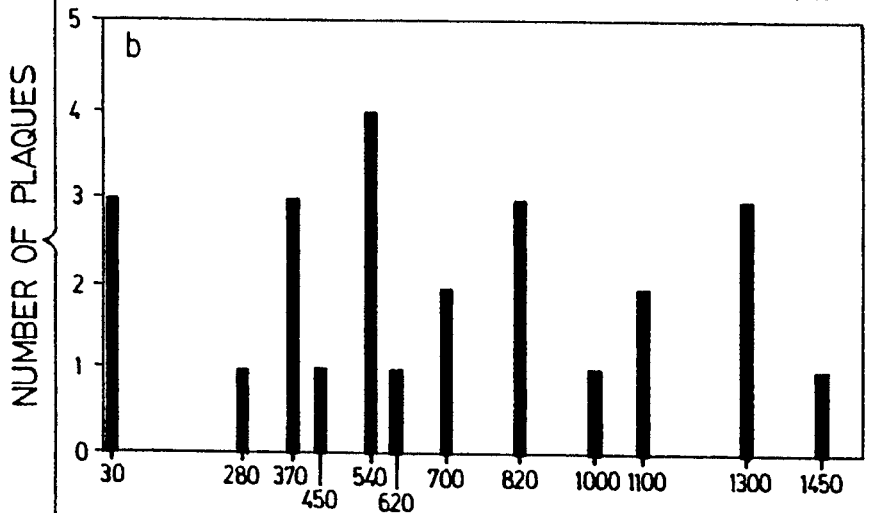
Figure 3C:
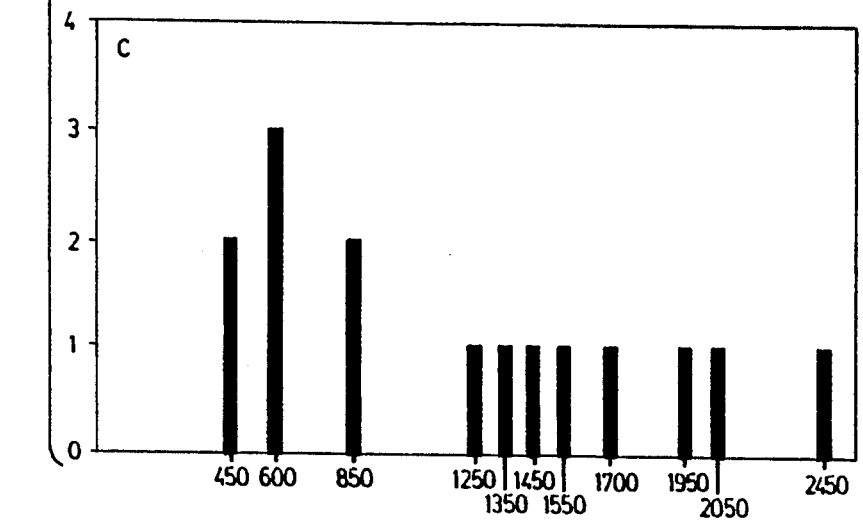

As FIGS. 3A, 3B and 3C show the distribution of deletion sizes is quite random. On only one occasion (FIG. 3A) was the distribution of the deletion clones slightly skewed towards the largest deletion clones, and thus was probably due to preferential deletion of secondary structures around that region.

Approximately 50% of the plaques analyzed on a 0.7% agarose gel had detectable deletions (Shen and Ways, 1988). When plaques were picked randomly and sequenced, 35% (six out of 17 clones) had lost the sequencing priming site. However, these clones could be eliminated readily by analyzing the sequence of one of the four nt. Ten out of eleven (90%) of these sequenced mutants which retained the sequencing priming site had the correct Junction as specified by the 10 nt of the 5' end of the oligodeoxynucleotide. Thus the overall percentage of deletion clones which were indeed unidirectional was approximately 60% (65%×90%/100). We have completely sequenced two of the deletion mutants containing the truncated tyrS gene using three sequencing primers along the gens separately by a method described by Wilkinson et al. (1984). No spurious mutation in the truncated gene was observed. In order to increase the low molar ratio of any particular sequence in the mixed oligodeoxynucleotides, 6 random nt were designed at the 3' end. A longer stretch of random nt would dramatically reduce the molar ratio. The use of another mixture of oligodeoxynucleotides which were longer (with 10 random nt: 5'-GGATCCC-CTANNNNNNNNNN-3', instead of 6 nt at the 3'end) did not offer any improvement.

REFERENCES

Carter, P., Bedouelle, H. and Winter, G.: Improved oligonucleotide site-directed mutagenesis using M13 vectors. Nucleic Acids Res. 13 (1985) 4431–4443.

Dale, R.M.K., McClure, B.A. and Houchins, J.P.: A rapid single-stranded cloning strategy for producing a sequential series of overlapping clones for use in DNA sequencing: application to sequencing the corn mitochondrial 18SrDNA. Plasmid 13 (1985) 31–40.

Gibson, T.J.: Studies on the Epstein-Bart Virus Genome. Ph.D. Thesis, University of Cambridge, Cambridge, U.K., 1984.

Guo, L.-H. and Wu, R.: New rapid methods for DNA sequencing based on exonuclease III digestion followed by repair synthesis. Nucleic Acids Res. 10 (1982) 2065–2074.

Hanahan, D.: Studies on transformation of *Escherichia coli* with plasmids. J. Mol. Biol. 166 (1983) 557–580.

Henikoff, S.: Unidirectional digestion with exonuclease III creates targeted breakpoints for DNA sequencing. Gene 28 (1984) 351–359.

Hong, G.F.: A method for sequencing single-stranded cloned DNA in both directions. Biosci. Rep. 1 (1981) 243–252.

Hong, G.F.: A systematic DNA sequencing method. J. Mol. Biol. 158 (1982) 539–549.

Messing, J., Gronenborn, B., Muller-Hill, B. and Hofschneider, P.H.: Filamentous coliphage M13 as a cloning vehicle: insertion of a HindIII fragment of the lac regulatory region in the M13 replicative form in vitro. Proc. Natl. Acad. Sci. USA 75 (1977) 3642–3646.

Messing, J.: A multipurpose cloning system based on the single-stranded DNA bacteriophage M13. Recombinant DNA Technical Bulletin, NIH Publication No. 79-99, Vol. 2, No. 2 (1979) 43–48.

Messing, J.: New M13 vectors for cloning. Methods Enzymol. 101 (1983) 20–78.

Moorman, A.F.M., De Boer, P.A.J., De Laaf, R.T.M., an Dongert, W.M.A.M. and Destree, O.H.J.: Primary structure of the histone H3 and H4 genes and their flanking sequences in a minor histone gene cluster of *Xenopus laevis.* FEBS Left. 136 (1981) 45–52.

Poncz, M., Solwiejczyk, D., Ballantine, M., Schwartz, E. and Surrey, S.: "Nonrandom" DNA sequence analysis in bacteriophage M13 by the dideoxy chain-termination method. Proc. Natl. Acad. Sci. USA 79 (1982) 4298–4302.

Sanger, F., Nicklen, S. and Coulson, A. R. DNA sequencing with chain-terminating inhibitors. Proc. Natl. Acad. Sci. USA 74 (1977) 5463–5467.

Shen, W. and Waye, M.M.Y.: A novel method for generating a nested set of unidirectional deletion mutants using mixed oligodeoxynucleotides. Gene 70 (1988) 205–211.

Turner, P.C., Aidridge, T.C., Woodland, H.R. and Old, R.W.: Nucleotide sequences of H1 histone genes from *Xenopus laevis.* A recently diverged pair of H1 genes and an unusual H1 pseudogene. Nucleic Acids Res. 11 (1983) 4093–4107.

Waye, M.M.Y. and Winter G.: A transcription terminator in the 5' non-coding region of the tyrosyl tRNA synthetase gene from *Bacillus stearothermophilus.* Eur. J. Biochem. 158 (1986) 505–510.

Waye, M.M.Y., Verhoeyen, M.E., Jones, P.J. and Winter, G. EcoK selection vectors for shotgun cloning into M13 and deletion mutagenesis. Nucleic Acids Res. 13 (1985) 8561–8571.

Wilkinson, A.J., Fersht, A.R., Blow, D.M., Carter, P. and Winter, G.: A large increase in enzyme-substrate affinity by protein engineering. Nature 307 (1984) 187–188.

Yanisch-Perron, C., Vieira, J. and Messing, J.: Improved M13 phage cloning vectors and host strains: nucleotide sequences of the M13mp18 and pUC19 vectors. Gene 33 (1985) 103–119.

We claim:

1. A process for preparing a set of truncated sequences of test DNA useful for dideoxy-sequencing, which comprises the steps:

inserting a test DNA sequence into a sequencing plasmid or phage vector, said sequencing vector containing in sequential order: a priming site for initiation of sequencing, an anchor site consisting of 5–200 nucleotide bases of predetermined identity, and a selection marker segment; the test DNA being inserted into the sequencing vector at a location such that the selection market segment is disposed between the inserted test DNA and the anchor site;

hybridizing a population of oligonucleotide probes to said sequencing vector, said probes comprising a nucleotide sequence composed of 5–200 nucleotide bases complementary to said anchor site of said sequencing vector linked to an additional sequence of random bases of at least 4 nucleotides;

replicating said sequencing vectors with annealed probe by deletion mutagensis so as to produce a population of deletion mutants of said sequencing vectors that lack the selection marker but contain randomly truncated sequences of said test DNA;

selecting for said deletion mutants by transforming bacterial cells incapable of tolerating the product of the selection marker of said sequencing vector with the deletion mutants of said replicating step.

2. The process of claim 1 wherein the random bases of the probes constitute the downstream (3') end and the predetermined bases constitute the upstream (5') end thereof, the anchor site and the 3. The process of claim 2 wherein the probes have a nucleotide sequence composed of 10-14 20 nucleotide bases, of which 5–10 bases are complementary to said anchor site and the remaining nucleotide sequence of the probes are composed of random bases.

4. The process of claim 3 wherein the probes have 16 total bases, of which six are random bases.

5. The process of claim 4 wherein the selection marker sequence is a marker of genetic intolerance.

6. The process of claim 5 wherein the selection marker sequence is EcoK or EcoB.

7. The process of claim 6 wherein the selection marker sequence is EcoK and the replication of the constructs with probes hybridized thereto takes place in cells having active EcoK restriction system which restricts propagation of constructs having EcoK sites.

8. The process of claim 1 wherein the plasmid or phage is a phagemid or M13 phage.

9. The process of claim 8 wherein the M13 phage is an M13K11RX construct or an M13K11 construct.

10. The process of claim 1 wherein the anchor site contains a stop codon or initiation codon for protein synthesis.

11. A kit for the preparation of deletion mutants from a sequencing vector containing target DNA comprising:

a sequencing plasmid or phage vector, said sequencing vector containing in sequential order: a priming site for initiation of sequencing, an anchor site consisting of 5–200 nucleotide bases of predetermined identity and sequence, and a selection marker segment, and at least one restriction site for the insertion of target DNA;

a population of oligonucleotide probes each probe comprising the same fixed nucleotide sequence being of predetermined sequence composed of 5–200 nucleotide bases complementary to said anchor site of said sequencing vector linked to an additional sequence of random bases of at least 4 nucleotides;

bacterial cells incapable of tolerating the product of the selection marker of said sequencing vector.

12. The kit of claim 11 wherein the random bases of the probes constitute the downstream (3') end and the 5–200 predetermined bases constitute the upstream (5') end; and wherein the components of the sequencing vector: the selection marker, the anchor site, and the priming site, are arranged sequentially in the downstream direction away from the test DNA insertion site.

13. The kit of claim 12 wherein the probes have from 10–20 nucleotide bases, of which 5–10 bases constitute the predetermined sequence and are complementary to the anchor site of the sequencing vector and the remaining nucleotide sequence of the probes are composed of random bases.

14. The kit of claim 13 wherein the probes have 16 total bases, of which 6 are random bases.

15. The kit of claim 14 wherein the sequencing vector selection marker sequence is a marker of genetic intolerance.

16. The kit of claim 15 wherein the selection marker sequence is Eco K or Eco B.

17. The kit of claim 11 wherein the sequencing vector has a polylinker sequence acting as sites for insertion of target DNA.

18. The kit of claim 17 wherein the viable bacterial cells have active Eco K or Eco B restriction systems which restrict propagation of constructs having Eco K or Eco B selection marker sequences respectively.

19. The kit of claim 18 wherein the sequencing vector is a phagemid or M13 phage.

20. The kit of claim 19 wherein the M13 phage is an M13K11RX construct or an M13K11 construct.

21. The kit of claim 11 wherein the sequencing vector has an anchor site containing a stop codon for protein synthesis.

* * * * *